(12) United States Patent
Gray

(10) Patent No.: US 8,894,976 B2
(45) Date of Patent: Nov. 25, 2014

(54) FLUORESCENT MEMBRANE INTERCALATING PROBES AND METHODS FOR THEIR USE

(75) Inventor: Brian D. Gray, Wayne, PA (US)

(73) Assignee: Phanos Technologies, Inc., Los Angeles, CA (US)

( * ) Notice: Subject to any disclaimer, the term of this patent is extended or adjusted under 35 U.S.C. 154(b) by 1197 days.

(21) Appl. No.: 12/094,251

(22) PCT Filed: Nov. 17, 2006

(86) PCT No.: PCT/US2006/044533
§ 371 (c)(1),
(2), (4) Date: Dec. 1, 2008

(87) PCT Pub. No.: WO2007/061768
PCT Pub. Date: May 31, 2007

(65) Prior Publication Data
US 2009/0304598 A1     Dec. 10, 2009

(30) Foreign Application Priority Data

Nov. 18, 2005    (AU) ................................ 2005234696

(51) Int. Cl.
| | |
|---|---|
| *A61B 10/00* | (2006.01) |
| *A61B 5/00* | (2006.01) |
| *A61B 8/00* | (2006.01) |
| *A61K 49/00* | (2006.01) |
| *C09B 23/01* | (2006.01) |
| *C09B 23/04* | (2006.01) |
| *C09B 23/06* | (2006.01) |
| *C09B 23/08* | (2006.01) |
| *G01N 33/58* | (2006.01) |

(52) U.S. Cl.
CPC ......... *A61K 49/0032* (2013.01); *C09B 23/0066* (2013.01); *C09B 23/04* (2013.01); *C09B 23/06* (2013.01); *C09B 23/083* (2013.01); *C09B 23/086* (2013.01); *G01N 33/582* (2013.01)
USPC ............ 424/9.6; 424/1.11; 424/1.65; 424/9.1

(58) Field of Classification Search
CPC .. C07D 263/00; C07D 413/00; C07D 277/00; C07D 277/60; C07D 277/62; C07D 277/68; C07D 317/00; C07D 317/08; C07D 498/00; C07D 513/00; C07D 209/00; C07D 209/04; C07D 209/10; C07D 209/56; C07D 405/00; C09B 23/00; C09B 23/0008; C09B 23/0016; C09B 23/0068; C09B 23/02; C09B 23/04; C09B 23/06; C09B 23/08; C09B 23/083; C09B 23/086; C09B 23/10; G01N 33/582
USPC ................... 424/1.11, 1.65, 9.1, 9.6, 9.7, 9.8; 548/146, 215, 300.1, 400, 469, 470; 430/581
See application file for complete search history.

(56) References Cited

U.S. PATENT DOCUMENTS

| | | | |
|---|---|---|---|
| 5,496,903 A | | 3/1996 | Watanabe et al. |
| 5,665,328 A | | 9/1997 | Horan et al. |
| 5,667,764 A | * | 9/1997 | Kopia et al. .................. 424/1.45 |
| 5,804,389 A | | 9/1998 | Tada |
| 6,004,536 A | * | 12/1999 | Leung et al. ................... 424/9.6 |
| 6,716,994 B1 | | 4/2004 | Menchen et al. |
| 7,462,347 B2 | * | 12/2008 | Gray .............................. 424/9.6 |
| 8,029,767 B2 | | 10/2011 | Gray |
| 2005/0009058 A1 | | 1/2005 | Lee et al. |

FOREIGN PATENT DOCUMENTS

| | | |
|---|---|---|
| JP | 2003-525915 A | 9/2003 |
| WO | 01/66153 A1 | 9/2001 |
| WO | WO 01/66153 * | 9/2001 |

* cited by examiner

*Primary Examiner* — D L Jones
(74) *Attorney, Agent, or Firm* — Rothwell, Figg, Ernst & Manbeck P.C.

(57) ABSTRACT

The invention relates to a family of dyes which fluoresce in the UV-VIS, far red and near infrared wavelengths of the spectrum and possess asymmetric lipophilic alkyl chains. The dyes of the invention are soluble in commercially available membrane staining dyes, are useful as probes for rapidly staining lipophilic structures such as membranes in cells or isolated from cells, and are well-retained therein. Methods of utilizing the dyes to detect stained cells both in vivo and in vitro are also disclosed.

17 Claims, No Drawings

FLUORESCENT MEMBRANE INTERCALATING PROBES AND METHODS FOR THEIR USE

FIELD OF THE INVENTION

The present invention relates to fluorescent, membrane intercalating compounds useful as dyes and probes. More particularly, the invention relates to lipophilic fluorescent compounds with an increased signal to noise ratio that are useful for rapidly labeling a variety of lipophilic particles or objects containing lipophilic structures, low density lipoproteins (LDL), high density lipoproteins (HDL), including cells, liposomes, microspheres and virus particles.

DESCRIPTION OF THE RELATED ART

It is known that fluorescent dyes have many uses and are particularly suitable for biological applications in which the high sensitivity detection of fluorescence is desirable. By binding to a specific biological ingredient in a sample, a fluorescent dye can be used to indicate the presence or the quantity of the specific ingredient in a sample. A variety of fluorescent dyes is available for fluorescent staining and such dyes are employed in quantitation of, e.g., cells, proteins, DNA and RNA. Fluorescent dyes are also employed for monitoring cellular trafficking in response to various physiological conditions. Such dyes have a wide range of applicability in both clinical and research applications where cell sorting and monitoring of cellular trafficking, proliferation and other responses are desired.

Fluorescent dyes are known to be particularly suitable for biological applications in which a highly sensitive detection reagent is desirable. Dyes that are able to preferentially bind to a specific biological ingredient or component in a sample enable the observer to determine the presence, quantity or location of that specific ingredient or component. In addition, specific biological systems can be monitored with respect to their spatial and temporal distribution in diverse environments. Cyanines are particularly advantageous for such applications, due to their high extinction coefficients and their amenability to the systematic selection of structural variations which give predictable shifts in excitation and emission properties. As a result, cyanines dyes have been used in various biological applications. The use of certain cationic lipophilic cyanine dyes, including $DiIC_{18}$ (3), $DiOC_{18}$ (3) and their $C_{12}$ to $C_{22}$ homologs in combination with an osmolarity regulating agent to stain cells for the purposes of labeling viable cells, tracking stained cells in vivo, and measuring cell growth rate has been previously described.

U.S. Pat. No. 4,762,701, which is incorporated herein by reference, refers to in vivo methods for tracking cyanine labeled cells that fluoresce in the visible regions of the spectrum and for determining cell lifetimes by measuring the rate at which the dye in labeled cells administered to a subject disappear.

U.S. Pat. No. 4,783,401, which is incorporated herein by reference, refers to methods for labeling viable cells with cyanine dyes that fluoresce in the visible regions of the spectrum in order to, among other things, measure the growth rate of cultured cells.

U.S. Pat. No. 4,859,584, which is incorporated herein by reference, refers to methods for determining the growth rate of cyanine labeled cells that fluoresce in the visible regions of the spectrum growing in vitro and in vivo.

U.S. Pat. No. 5,804,389, which is incorporated herein by reference, refers to methods for determining abnormal cell shedding rates by labeling cell membranes with cyanine dyes that fluoresce in the visible regions of the spectrum and observing the rate at which the labeled cells are shed from the mucosal surface.

U.S. Pat. No. 6,004,536 to Leung et al., the teachings of which are also incorporated by reference herein in their entirety, refers to cyanine dyes possessing two lipophilic alkyl chains that are preferably equal in length and incorporate either a reactive functional group, or a phenyl, sulfo, sulfophenyl, or a bromo or chloro substituent that are useful for staining lipophilic structures, such as membranes in cells or tissues, membranes isolated from cells, natural or artificial liposomes, lipoproteins or polymers. Leung et al. teaches that the dyes are preferably soluble in an aqueous environment.

Flow cytometry and fluorescence activated sorting have been used extensively to separate different classes of cells in the cell populations in blood and in bone marrow. Such methods have been particularly useful to separate the different types of leukocytes from each other, as a tool in typing of leukemias and lymphomas (See e.g., U.S. Pat. No. 5,234,816), and to obtain blood stem cell progenitor fractions isolated away from other cell types (U.S. Pat. No. 5,137,809, Aug. 11, 1992), for research and for therapeutic uses. Flow cytometers have become routine in clinical laboratory use. Several parameters of a cell may be measured simultaneously: forward scattered light is used to measure cell size; and a second scatter detector provides information on the granularity of the cell cytoplasm, used to differentiate the various types of leukocytes. Fluorescent light emitted from various "fluorochromes," each of which is bound to a specific cellular target molecule, is collected by the cytometer. These parameters create a broad range of applications dependent on the specificity and combination of a dye-conjugated molecules and its target.

Although cytometry today relies upon correlated analysis of 3-4 color data, the field is rapidly moving toward use of more probes/cell to dissect complex inter and intracellular events by analyzing the characteristics of various subpopulations of cells in complex mixtures (as, e.g., in a developing immune response). The nature of excitation and emission characteristics of fluorochromes makes it difficult to select more than three or four visible emitting fluorochromes attachable to cells which provide emissions sufficiently separated in wavelength to give good spatial and/or spectral discrimination.

General labeling of cell proteins or membranes with stable fluorescent probes is also a powerful method for delineating intricate cell-cell interactions, as for example when analyzing immune system functions. However, currently available protein and membrane labels, such as CFSE (Molecular Probes) and the PKH dyes (Sigma), have significant limitations when studying cellular interactions and responses both in vivo and in vitro. Because they excite and fluoresce in the visible regions of the spectrum, high levels of tissue scattering and autofluorescence can render such dyes unsuitable for optical imaging in intact animals. In addition, cellular autofluorescence limits the signal:noise (S/N) ratio that can be achieved and significant spectral overlap with other commonly used visible fluors complicates instrument setup when such dyes are used for flow cytometry or confocal microscopy. Although longer wavelength analogs of DiO and DiI that are applicable to general membrane staining are known in the art, time as well as concentration must be varied to achieve optimum staining with these dyes.

The complex cell types, trafficking and localization patterns, signaling mechanisms, and regulatory feedback loops which constitute the innate immune system allow it to respond highly selectively to a particular antigen or pathogen and also offer the potential to selectively enhance or interfere with a response. However, this selectivity is achieved primarily based on localized encounters involving antigen, antigen presenting cells, and lymphocytes in the context of tissue specific adhesion molecules and secreted molecular messengers such as chemokines and cytokines. Therefore, productive intervention in the immune surveillance and response process requires the ability to dissect and monitor complex cellular interactions in vitro, ex vivo, and in vivo. The ability to selectively tag different cell types and follow their fate is critical to understanding immune responses in sufficient detail to design and optimize effective treatment strategies involving immunotherapy.

General membrane labeling with fluorescent lipophilic dyes which intercalate stably into cell membranes is simple, rapid, and applicable to almost any cell type. Currently available probes of this type have been utilized for purposes of tracking and identifying specific cell types and they offer several advantages in contrast to utilizing general protein labeling for such purposes. Since labeling is non-covalent and occurs by partitioning into the lipid bilayer, there is no waiting period for fluorescent intensity to stabilize, such as is required for covalent protein labels (e.g., CFSE), and untoward effects on cellular receptor-ligand interactions and associated responses are typically minimal.

The most common fluorophores used to label cells and biomolecules were originally developed for microscopy, and for reasons of compatibility with available light sources and the human eye, fluoresce primarily in the UV and visible regions of the spectrum (approximately 400 to 600 nm). Dilution of membrane intercalating dyes among daughter cells has proven very useful for monitoring differential cell proliferation responses in complex populations and for tracking of cells in responding to stimuli such as antigenic challenge. Like general protein labels, concentration of membrane dyes is halved with each cell division, thus limiting use for long term tracking. Also, in both general protein labeling and fluorescent membrane labeling, high labeling intensity (often 1-2 orders of magnitude greater than bright antibody labeling) can complicate filter selection and color compensation when used in combination with other probes.

The above challenges and limitations to fluorescent labeling have brought increasing interest in development of fluors that excite and emit in the FR and NIR wavelengths. Although usage in the literature varies considerably, we here define FR as 600-700 nm and NIR as 700-900 nm, since water absorption and thermal background begin to interfere with measurement of biological fluorescence at >900-1000 nm. The use of FR or NIR fluors has a number of significant advantages in biological systems in general, and for cellular analysis in particular. These include i) decreased background caused by tissue or protein autofluorescence, ii) decreased background caused by Raman scatter, iii) less spectral overlap when used in conjunction with common UV or visible fluors, and iv) excitation and emission profiles compatible with the use of inexpensive excitation sources (e.g. diode lasers) and detectors (e.g. avalanche diodes). FR fluorescing analogs can be used on existing flow cytometers and confocal microscopes, since many of these instruments have FR excitation capability (HeNe, 635 nm diode, or 647 nm Kr/Ar lasers). Use of FR analogs therefore provides i) ability to do longer term in vitro and in vivo tracking of dividing cells due to reduced background and improved signal/noise ratio and ii) simpler instrument setup due to reduced spectral overlap.

Utilization of NIR fluorescence has significant advantages over even FR imaging for in vivo optical imaging of intact tissues or animals. In addition to decreased background from autofluorescence and Raman scattering, NIR light is better transmitted in vivo and thus real time fluorescence imaging can be performed through millimeters to centimeters of tissue. In fact, the longer the wavelength of the exciting light or the NIR fluorescence, the better the tissue penetration, due to reduced elastic scattering and the fact that the few biomolecules which absorb in this region (hemoglobin and deoxyhemoglobin) do so only weakly. FR and NIR labeled antibodies or polymers have been shown to enhance contrast between normal tissue and tumors. Current depth of detection is in the 0.5-1 cm range but NIR light can travel through tissue for 5-6 cm.

It is known that adjusting the composition of aromatic groups and the number of methine groups separating the aromatic groups of cyanine dyes causes changes in the light excitation and emission patterns and color of these dyes. In general, increasing the number of methine groups separating aromatic components of the dyes will shift the emission spectra toward the red and near infrared wavelengths. Increasing the length of the methine bridge between aromatic groups, however, also increases the overall liphophilicity of the aqueous solubility to be compatible with sensitive biological materials (e.g., cells) while minimizing the negative impact of standard physiological media and salts on the lipophilic substances.

SUMMARY OF THE INVENTION

Accordingly, the present invention is directed to novel membrane intercalating dyes (also referred to herein as "probes") that fluoresce in the far red, near infrared, green and UV-VIS range segments and are soluble in commercially available membrane staining diluents. These probes are useful in diagnostic applications and, potentially, photodynamic therapy. The present invention is also directed to compositions containing the probes in aqueous and non-aqueous labeling vehicles suitable for staining biological materials.

In another aspect, the invention provides methods of contacting the probes with cells and/or other lipophilic structures, allowing the probes to intercalate with the lipophilic structures, and detecting the cells or other lipophilic structures in vitro and or in vivo based on the fluorescence emitted therefrom.

In a preferred embodiment, the invention is directed to a method of labeling epithelial cells in vivo with cyanine dyes to provide an in vivo method for diagnosing disease states which are characterized by the presence of abnormal cell shedding rates amongst mature epithelial cells.

To achieve these and other objects, the present invention provides an in vivo method for detecting abnormal cell shedding rates among mature epithelial cells, such as epithelial cells of mucosal surfaces, of a warm-blooded animal comprising the steps of labeling mature surface epithelial cells at a target site with UV-VIS, FR and NIR probes and thereafter monitoring the site for the presence or absence of label.

In another embodiment, the cells which are labeled reside on mucosal surfaces, among which mucosal surfaces of the gastrointestinal tract provide particularly preferred targets. The present invention also provides a method for diagnosing disease states characterized by abnormal cell shedding rates among mature epithelial cells of a warm-blooded animal, comprising labeling mature epithelial cells with the UV-VIS, FR and NIR probes of the invention, determining the shedding rate of the labeled cells and comparing the shedding rate of the labeled cells to the known shedding rate of similarly located healthy epithelial cells.

DESCRIPTION OF THE PREFERRED EMBODIMENTS

Reference will now be made in detail to the presently preferred embodiments of the invention. The invention provides compounds that are novel membrane intercalating dyes (also referred to herein as "probes") that fluoresce in the UV-VIS, far red and near infrared segments of the spectrum and methods for their use. The invention also provides labeling compositions comprising the probes solubilized in a labeling vehicle. The probes are solubilized in a vehicle compatible with the biological and/or solvent sensitivities.

The compounds contain lipophilic tails (referred to herein in the structures as "R" and "R'" that in some embodiments are equal in length while in some preferred embodiments, R≠R'.

It is contemplated that the probes of the present invention may be used in conjunction with other labeling techniques and reagents for multiparameter cell tracking and sorting procedures. Usefulness of a dye in combination with others is traditionally determined by two aspects of spectra of light energy interactions: (1) the extent to which a dye molecule is excited by a single illumination wavelength or narrow band of wavelengths and (2) the extent to which each excited dye molecule emits light of wavelength sufficiently different from the other dyes so as to be discernible as a unique color or peak. The first aspect enables the user to illuminate the multiply-stained biological sample with a single wavelength and the second aspect enables the user to observe and record different colors of emission, each of which is associated with a particular cell type or a structure.

There are a number of new detectors under development in which the entire spectrum of light is collected and then the curves characteristic of each probe's emission are devolved from the aggregate signal taken over the entire spectrum. It is also contemplated that the probes of the present invention will be readily detected using such instruments.

The probes of the invention, when used as membrane-intercalating dyes selectively stain cell membranes in vitro, ex vivo and in vivo and do not undesirably affect the nature of the cells. The probes and thus the cells or other lipophilic structures to which they become attached can be readily identified by the fluorescence they emit. In addition, the compounds of the present invention are not cytotoxic when used at appropriate concentrations, are stably retained in cell membranes, and stain cells rapidly. The probes need only be applied to cells for a few minutes to achieve staining intensities 100-1000 times greater than background autofluorescence. Another beneficial aspect of the compounds of the present invention is that they are soluble in isotonic salt free diluents suitable for membrane labeling such as Diluent C (Sigma-Aldrich Corporation). The probes of the present invention are useful generally as agents for cell labeling, cell sorting and cell tracking in vitro and in vivo for both basic (laboratory) and clinical research. For examples of such uses, see U.S. Pat. Nos. 5,385,822; 5,256,532, the disclosures of which are incorporated by reference herein; and U.S. Pat. Nos. 4,859,584; 4,783,401 and 4,762,701. Such probes will be useful, for example, as research reagents for use in existing flow cytometers and confocal imaging systems which have FR and/or NIR capabilities.

The probes of the present invention will 1) bind to cells in sufficient numbers to give a good signal compared to autofluorescence; 2) not be toxic to the cells at that level, and 3) be retained in the cell membrane long enough for tracking and/or sorting of particular subgroups of cells to be completed.

The lipophilic nature of the probes of the present invention provides for the efficient incorporation of the probes into various lipid containing or hydrophobic structures, including cell and viral membranes, liposomes, microspheres and the like. When incorporating the probes into cells and virions, a labeling composition comprising the probe and an aqueous labeling vehicle is mixed with the target to be labeled. The labeling composition contains a cyanine dye in a vehicle (diluent) that is safe for application and that provides reproducible cell labeling. Osmolarity regulating agents in which cyanine dyes form stable solutions for at least as long as required for labeling can be used. Acceptable osmolarity regulating agents may be selected from sugars including monosaccharides such as glucose, fructose, sorbose, xylose, ribose, and disaccharides such as sucrose; sugar-alcohols including mannitol, glycerol, inositol, xylitol, and adonitol; amino acids including glycine and arginine; and certain Good's buffers such as N-tris(hydroxymethyl)-methyl-3-aminopropanesulfonic acid. Small amounts of buffering agents may be added to the labeling medium to regulate hydrogen ion concentration (pH) to physiological and/or non-toxic levels. Other conventional agents, such as antibiotics and preservatives, may be also be employed in the vehicle, but only to the extent that they do not create salt concentrations that induce rapid formation of dye micelles or aggregates.

When incorporating the probes into microspheres or liposomes and like materials which can tolerate exposure to non-aqueous labeling vehicles without detrimental effect, a labeling composition comprising the probe and a non aqueous aqueous labeling vehicle is mixed with the target to be labeled. Non aqueous labeling vehicles include polar organic solvents such as ethanol, dimethyl formamide, dimethylsulfoxide, and the like.

Despite their lipophilic nature, we have found that the probes of the present invention are sufficiently soluble in aqueous vehicles to allow efficient and rapid staining of lipophilic structures (membranes and the like) which are detrimentally affected by exposure to polar organic solvents.

Research shows that good solubility in DMF is advantageous for indirectly labeling distant cells in tissue preparations by coating high concentrations of dye on filter nylon falters and inserting them into tissue. See B. Fritzch et al., *Brain Res. Bull.*, 66 249-258 (2005).

The detection step can employ a luminescence microscope or other optical imaging apparatus such as e.g., a fiber optic diagnostic device such as a cystoscope or endoscope and the like, having a filter for absorption of scattered light of the excitation wavelength and for passing the wavelength that corresponds to the fluorescence corresponding to the particular dye label used with the specimen. Preferred methods of observation and analysis include direct visualization with a microscope fitted with a light source and filters appropriate to the excitation and emission wavelengths, and use of a camera attached thereto.

A preferred method of the invention for cell separation and enumeration of live cells appropriately stained with this class of probe reagents, is by use of a flow cytometry apparatus such as a FACSCalibur analyzer or FACSVantage cell sorting instrument. These instruments illuminate a mixed cell population, for example at a given wavelength with an argon laser source of light, and use an emission signal from each cell detected in a moving fluid such as a buffer, to sort each cell as it is flowing past the detector using a variety of bandpass filters for collection of emitted light using techniques well known in the art. The apparatus can count and/or collect cell populations yielding both data and cell fractions for further analysis and use.

In another preferred embodiment, cells are labeled with the probes of the present invention and one or more additional cell markers which also bind to the labeled cells. The probes and the additional cell markers are then detected by flow cytometry. Alternatively, markers may be selected that recognize cells not labeled with the probes of the present invention. Detection of multiple markers in addition to or instead of the probes of the present invention enables identification and/or separation of specific subgroups of cells based on multiple phenotypes. Many additional cell markers such as fluorescent-labeled monoclonal antibodies specific for individual cell surface ligands and the like are known in the art.

Recent advances in technology have made it possible to do fluorescence imaging not only at the microscopic (cellular and subcellular) level but also at the macroscopic (whole tissue or whole body) level. The probes of the present invention provide useful solutions to the problem of spectral "pollution" or spill, which is frequently encountered when doing multiprobe studies using confocal imaging or other quantitative microscopy techniques. In addition, the NIR probes, when combined with macroscopic imaging methods, provide a useful alternative to radiolabels for monitoring immune cell trafficking, localization and redistribution in intact animals as well as potential for use in photodynamic diagnosis and/or phototherapy.

In another preferred embodiment, the probes of the present invention are administered to a subject for detection of abnormal epithelial cell shedding rates in vivo such as described in U.S. Pat. No. 5,804,389. In this process, the abnormal shedding of epithelial cells in a warm-blooded animal is determined. The process includes the steps of labeling mature surface epithelial cells with the compounds of the present invention at a target site, exposing the cells to light of an excitation wavelength and thereafter monitoring the site for the presence or absence of the label, and observing by the loss of detectable label over a pre-defined period of time. The present invention also provides a method for diagnosing disease states characterized by such abnormal cell shedding rates amongst mature epithelial cells of a warm-blooded animal, comprising labeling mature epithelial cells, determining the shedding rate of the labeled cells and comparing the shedding rate of the labeled cells to the known shedding rate of similarly located healthy epithelial cells.

The probes of the present invention can be utilized to determine abnormal shedding rates on any epithelial surface of the body. Surfaces include those of the stomach, biliary tract, colon, urinary tract, blood vessels, pulmonary tract including the nasal cavity, cornea, esophagus, pancreatic duct, small intestine, and genital organs including the vagina and ovarian duct and the prostate gland. Preferably, the composition in solution form is administered by direct application (e.g. spraying) onto the surface of the epithelial mucosa under direct vision by endoscope, by flooding the surface with a solution, or by orally administering the solution to the subject in the form of a drink.

When in vivo use in humans is contemplated, a solution of any of the compounds of the present invention can be prepared by dissolving an effective amount of the probe in an iso-osmotic, aqueous and preferably salt-free solvent miscible with both water and polar organic solvents. The concentration levels of dyes in compositions for in vivo use according to the present invention will be similar to the concentration levels used in the previously-known in vitro cell staining applications of those dyes. The precise concentration to be administered can be varied and can be readily optimized. The volume of probe composition to be administered will vary depending upon the concentration of the cyanine dye in the composition and upon the size of the target site. The administration volume may vary, for example, from about 1 to 100 ml and can be readily optimized. An administration volume of about 10 ml of the probe composition can be used in many applications. Administration route will vary depending upon the type of cells to be labeled. As indicated above, for staining of epithelial cells may be best achieved by oral administration or direct application. Other modes of administration, such as subcutaneous, intramuscular and intravenous injection and the like are also contemplated.

According to the preferred method of the invention, the cyanine dye label is detected by exposing the site of labeled cells to excitation light and observing and/or measuring the intensity of the fluorescence.

The probes of this invention can be synthesized, as set forth in detail in the examples below.

The UV-Vis, FR and NIR probes of the present invention can be detected by commercial cytometry instrumentation with the ability to excite fluors which absorb in the 400-700 nm range and emit in the UV-VIS range from 400-600 nm, FR from 600-700 nm and NIR >700 nm range (e.g., BD FACS-Vantage, FACSCalibur, Beckman Coulter Altra, and Cytomation MoFlo flow cytometer/sorters, and BioRad 1024ES or 1024 MP confocal imaging systems). The advent of small benchtop cytometers (e.g. volume capillary cytometer in development by Biometric Imaging/BD which incorporate inexpensive diode lasers and diode detection systems will provide additional detection systems to quantify NIR fluorescence.

This near infrared/far red wavelength also is advantageous in that the background fluorescence in this region normally is low in biological systems and high sensitivity can be achieved.

A preferred labelling composition of the present invention comprises a cyanine dye of the formula:

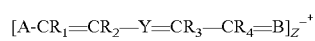

wherein "—Y—"
is selected from the group consisting of
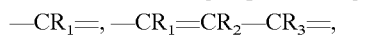
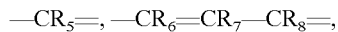
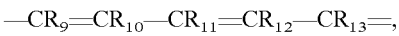
and

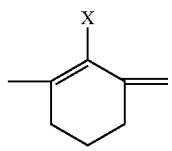

wherein each of $R_1, R_2, R_3, R_4, R_5, R_6, R_7, R_8, R_9, R_{10}, R_{11}, R_{12}$, and $R_{13}$ is dependently H, halogen or an alkyl group having 1-4 carbons;

X is selected from the group consisting of H, halogen, O-alkyl, O-aryl, S-alkyl and aryl;

Z is a biologically compatible counterion;
"A-"
a structure selected from the group consisting of

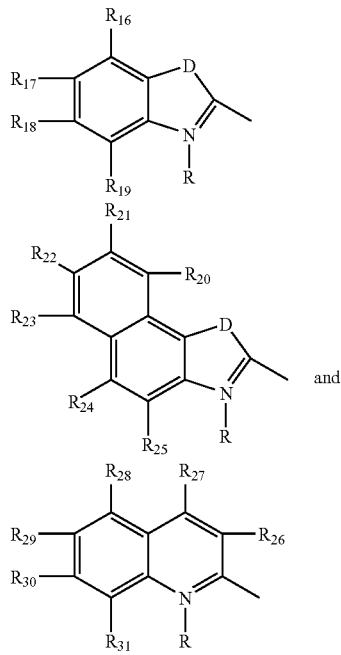

and "=B"
is selected from the group of structures consisting of

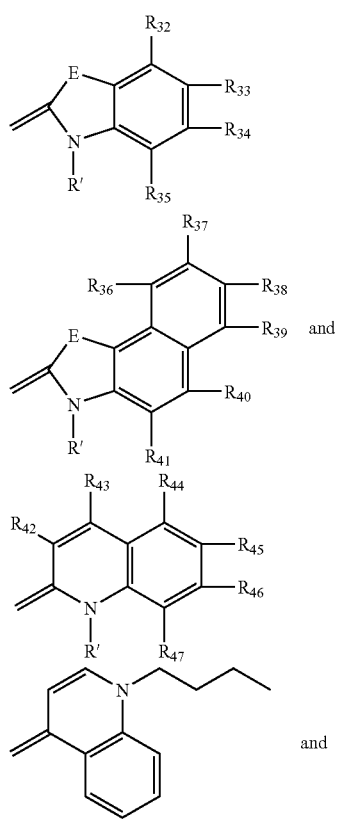

and

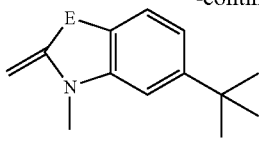

wherein D and E are each independently O, S or $CR_{14}R_{15}$, where $R_{14}$ and $R_{15}$, which may be the same or different, are independently alkyl groups having 1-6 carbons. Alternatively, $R_{14}R_{15}$ taken in combination complete a 5- or 6-membered saturated ring. Preferably X equals Y (yielding a symmetrical cyanine). In some preferred embodiments, both D and E are $CR_{14}R_{15}$, where $CR_{14}R_{15}$ are methyl or ethyl, more typically methyl.

Each of $R_{16}$-$R_{47}$ is independently H, halogen, phenyl (optionally substituted with halogen, cyano, and nitro), phenylsulfonate, $NO_2$ or an alkyl group of 1-4 carbons.

R and R' are each independently linear or branched hydrocarbons, saturated or containing unsaturated double bonds having 7-36 carbons, with the proviso that one of R and R' must be at least 3 carbons.

Z is a counterion that is typically an anion that balances the intrinsic positive charge of the cyanine dye and is present in such a number and with such a total charge as to make the overall molecule electrically neutral. As used herein, a substance that is biologically compatible is not toxic as used, and does not have a substantially deleterious effect on biomolecules. Such compounds also must not undesirably affect cell viability in the concentrations required for labeling. Accordingly, pharmaceutically acceptable forms of the cyanine dye other than the iodide salt may be employed in some instances, including other pharmaceutically acceptable salts. Examples of useful counterions for dyes having a net positive charge include, but are not limited to, chloride, bromide, iodide, sulfate, alkanesulfonate, arylsulfonate, phosphate, perchlorate, tetrafluoroborate, nitrate and anions of aromatic or aliphatic carboxylic acids. Selection of an appropriate anion, however will be limited by the particular anions' affect on solubility, since it is known that the anion associated with the various lipophilic molecules can effect the solubility of the compound.

In a preferred embodiment, the counter ion is iodide. In certain instances, such as for in vivo administration of the probes, it may be preferable to substitute the iodide counterion with a chloride, since some individuals are allergic to iodine.

The present invention is further described in the following examples which are provided for illustrative purposes only and are not to be construed as limiting. Standard techniques well known in the art or the techniques specifically described below are utilized.

EXAMPLE 1

Synthesis of Unsubstituted FR Cyanine Dyes
F279A, F280A, F283A, F284A, F285A, F299A,
F300A with Approximately 665 nm Emissions These membrane probes with the above-referenced emissions were prepared using the same generic synthetic scheme and reaction conditions as described below using the appropriate alkyl iodide or alkyl 4-chlorobenzene sulfonate ester or unsaturated alkyl 4-chlorobenzene sulfonate ester to provide the required hydrocarbon tail length.

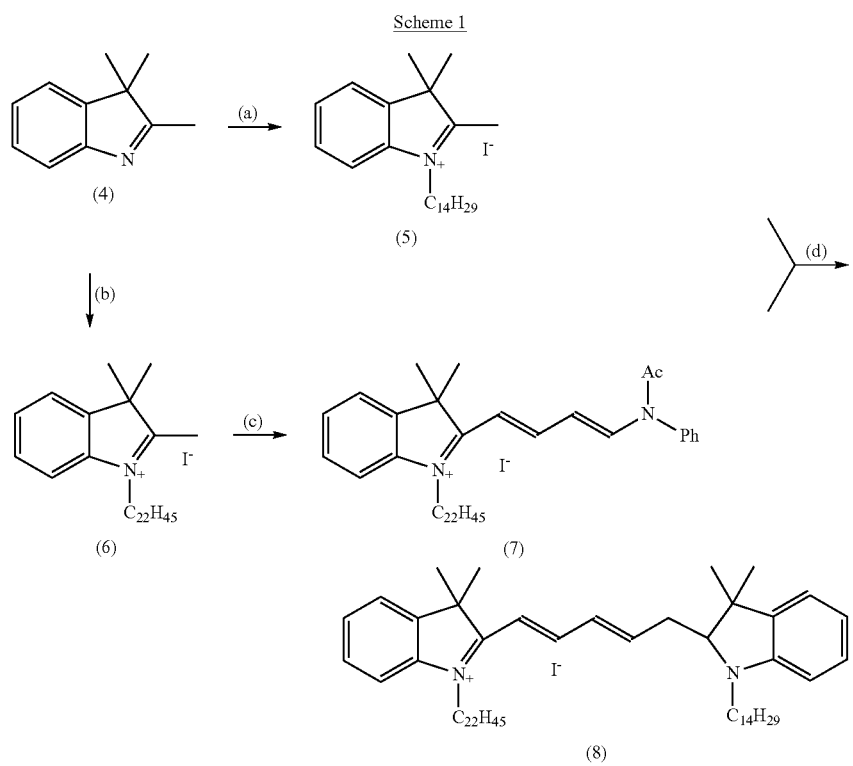

Scheme 1

Preparation of 1-tetradecyl-2,3,3-trimethylindolinium Iodide (compound 5) was carried out according to the following protocol. Tetradecyl-1-(4-chlorobenzenesulfonate): To a stirred solution of tetradecanol (26.3 g, 0.123 mol, Aldrich Chemical Co., Milwaukee, Wis.) and 4-chlorobenzenesulphonyl chloride (28.48 g, 0.123 mol, Aldrich) in dichloromethane (500 ml) at room temperature is added triethylamine (28 ml, Aldrich) in dichloromethane (200 ml) dropwise. The resulting solution is stirred for 48 hours. The reaction mixture is then washed with water (3×400 ml) and the dichloromethane layer dried over sodium sulfate and concentrated. The crude solid obtained was recrystallized from methanol to provide pure tetradecyl-1-(4-chlorobenzenesulphonate) (29.9 g, 62%) as a white solid. 200 MHz proton NMR (CDCl$_3$): 0.88 (t, Jm 7.0 Hz, 3H), 1.10-1.80 (m, 24H), 4.05 (t, J=7.0 Hz, 2H), 7.50-7.60 (m, 2H), 7.80-7.90 (m, 2H).

2,3,3-trimethyl-(3H)-indolene (4) (6.36 g, 0.04 mol, Aldrich) and tetradecyl-1-(4-chlorobenzenesulfonate) (15.52 g, 0.04 mol) are heated together with stirring at 130-140° C. for 3 h. The reaction mixture is then cooled to room temperature and dissolved in ethanol (200 ml). A saturated solution of potassium iodide (200 ml) is added and this mixture is stirred for 30 mins. 1.5 L of distilled water is then added and after a further 15 minutes stirring, the solid precipitate is collected, washed with water and dried under vacuum. The crude material is recrystallized from ethyl acetate to provide pure intermediate compound 5 (11.9 g, 62%). 300 MHz proton NMR (CDCl$_3$): 0.88 (t, J=7 Hz, 3H), 1.25-1.50 (m), 1.67 (s, 6H), 1.93 (m, 2H), 3.13 (s, 3H), 4.70 (t, J=7.70 Hz, 2H), 7.60-7.66 (m, 4H).

Preparation of
1-docosanyl-2,3,3-trimethylindolinium Iodide (6)

Docosanyl-1-(4-chlorobenzenesulfonate); To a stirred solution of docosanol (47.8 g, 0.15 mol) and 4-chlorobenzenesulphonyl chloride (34.01 g, 0.16 ml, Aldrich) in dichloromethane (500 ml) at room temperature is added triethylamine (33.5 ml, Aldrich) in dichloromethane (200 ml) dropwise. The resulting solution is stirred for 48 h. The reaction mixture is then washed with water (3×400 ml), the organic layer dried over sodium sulfate and concentrated to ~400 ml to initiate crystallization of the product. After cooling and aging the precipitate is collected by filtration and dried under vacuum to provide pure docosanyl-1-(4-chlorobenzenesulphonate) (48.9 g, 73%) as a white solid. 300 MHz proton nmr (CDCl$_3$): 0.88 (t, J=7.0 Hz, 3H), 1.15-1.40 (m), 1.55-1.75 (m, 2H), 4.02 (t, J=7.0 Hz, 2H), 7.48-7.60 (m, 2H), 7.78-7.90 (m, 2H).

2,3,3-trimethyl-(3H)-indolene (6.3 g, 0.04 mol, Aldrich) and docosanyl-1-(4-chicrobenzenesulfonate) (20.0 g, 0.04 mol) are heated together with stirring at 130-140° C. for 3 h. The reaction mixture is then cooled to room temperature and the waxy solid dissolved in ethanol (250 ml). A saturated solution of potassium iodide (200 ml) is added and this mixture stirred for 30 mins. 1.0 L of distilled water is then added and after a further 15 minutes stirring, the solid precipitate is collected, washed with water and dried under vacuum. The crude material is recrystallized from dichloromethane/hexane to provide pure intermediate compound 6 (14.5 g, 61%). 200 MHz proton NMR (CDCl$_3$): 0.87 (t, J=7.0 Hz, 3H), 1.15-1.50 (m), 1.67 (s, 6H), 1.85-2.00 (m, 2H), 3.10 (s, 3H), 4.70 (t, J=7.7 Hz, 2H), 7.55-7.70 (m, 4H).

Preparation of 1-docosanyl-2-[(4-N-phen-N-acetylamino)-1,3-butadienyl]-3,3-dimethylindolinilim iodide (7)

A solution of (6) (2-38 g, 4 mmol) and malonaldehyde bisphenylimine hydrochloride (1.10 g, 4.4 mmol, TCI America, Portland, Oreg.) in acetic anhydride (30 ml) is heated at 100-110° C. for 1 h, cooled to room temperature and filtered. The filtrate is then diluted with 300 ml of water and placed in a refrigerator at 0-5° C. for h. The resulting precipitate is collected and dried under vacuum to provide (7) (0.65 g, 21%). 300 MHz proton NMR (CDCl$_3$): 0.88 (t, J=6.5 Hz, 3H), 1.20-1.40 (m), 1.70 (m), 1.80 (s, 6H), 2.24 (s, 3H), 4.36 (t, J-z 7.5 Hz, 2H), 5.79 (t, Jm 12.8 Hz, 1H), 6.71 (d, J=15.0 Hz, 1H), 7.25-7.70 (m, I OH).

Intermediate compound 7 (0.544 g, 0.71 mmol) and intermediate 5 (0.343 g, 0.71 mmol) are heated together in refluxing dichloromethane (10 ml) containing 10 drops of triethylamine for 3 h. The reaction is monitored by TLC (5% methanol in dichloromethane). The reaction mixture is then concentrated by rotary evaporation and the residue crystallized from methanol at −20° C. overnight. The solid is collected and purified further by silica gel flash column chromatography eluting with 5-7.5% methanol in dichloromethane. Pure fractions are combined and concentrated to provide compound 8 (210 mgs, 30%). Purity >97% by HPLC. 300 MHz proton NMR (CDCl$_3$): 0.88 (t, J=6.3 Hz, 6H), 1.25-1.55 (m), 1.66 (m), 1.81 (s, 16H), 4.04 (t, J=7.4 HZ, 4H), 6.29 (d, J=13.6 Hz, 2H), 6.78 (t, J=12.4 Hz, 1H), 7.05 (d, J=7.8 Hz, h.), 7.20-7.70 (m, 2H), 7.33-7.38 (m, 4H), 8.32 (t, J=13.0 Hz, 2H). Electrospray mass spectroscopy. M'=860. UV/VIS (ethanol): λmax=648 nm, c=189,270 M-1 cm-1. Fluorescence (ethanol): excitation max.=653 nm, emission max.=672 nm.

Probe with this emission wavelength was selected for synthesis because it is red shifted by >100 nm compared with most other visible fluorescent probes used for cell labeling and there-fore has minimum spectral overlap with them. Such probe could therefore be ideal for use in flow cytometry and confocal microscopy when multiprobe labeling is required. Varying alkyl chain lengths can be incorporated as needed to adjust strength/stability of membrane association.

EXAMPLE 2

Synthesis of FR Probe F288A

This compound is prepared as shown in Scheme 1 above using similar types of reactions and conditions but using 5-tert-butyl-2,3,3-trimethyl(3H)indolenine as the starting material.

EXAMPLE 3

Synthesis of FR Probe F289A a. This compound is prepared as shown in Scheme 1 above using similar types of reactions and conditions but using 5-bromo-2,3,3-trimethyl(3H)indolenine as the starting material.

EXAMPLE 4

Synthesis of NIR Probe F277A

This compound is prepared as shown in Scheme 2 below, using similar types of reactions and conditions to those already described above.

EXAMPLE 5

Synthesis of NIR Probe F301A a. This compound is prepared as shown in Scheme 2 below, using similar types of reactions and conditions to those already describe above but using 2,3,3-trimethyl(3H)indolenine as the starting material.

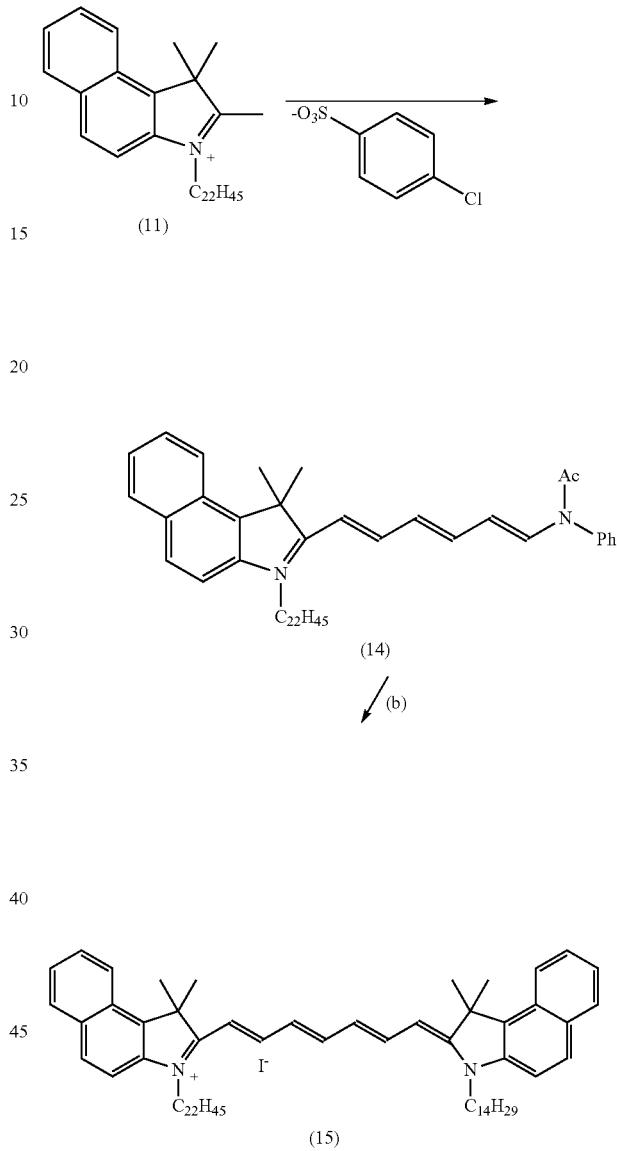

EXAMPLE 6

Synthesis of NIR Probes F291A

This compound is prepared as shown in Scheme 3 below, using similar types of reactions and conditions to those already describe above but using 2,3,3-trimethyl(3H)indolenine as the starting material and displacing the chloro functionality on the bridging cyclohexene ring with a thiophenyl group upon reaction with sodium benzthiolate in dimethylformamide at room temperature.

Scheme 3

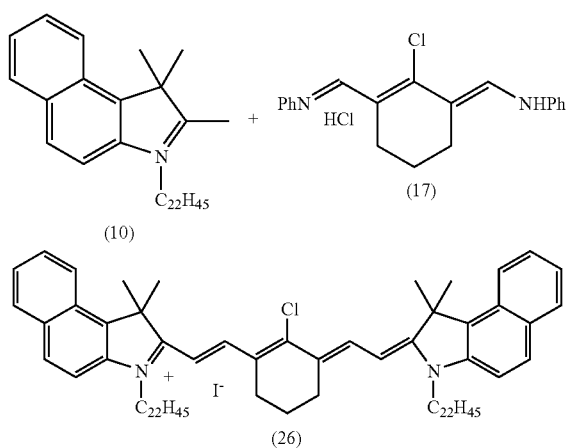

Intermediate 17 was prepared in 28% yield from cyclohexanone according to techniques known in the art. The optimal conditions for coupling of 17 with 2 mole equivalents of 10 is reflux in ethanol containing sodium acetate. The resulting compound is treated with potassium iodide followed by purification using silica gel chromatography.

EXAMPLE 7

Synthesis of Probe F295B

This compound is prepared as shown in Scheme 1 above using similar types of reactions and conditions but using 6-phenyl-2,3,3-trimethyl(3H)indolenine as the starting material for one side of the headgroup and 2,3,3-trimethyl(3H) indolenine for the other side.

EXAMPLE 8

Synthesis of Probe F296B

This compound is prepared as shown in Scheme 1 above using similar types of reactions and conditions but using 6-phenyl-2,3,3-trimethyl(3H)indolenine as the starting material for both sides of the headgroup.

EXAMPLE 9

Synthesis of Probe F297B

F297B was prepared from F295B, upon treatment with 20% fuming sulfuric acid in a solution of concentrated sulfuric acid. Yields were 65%.

EXAMPLE 10

Synthesis of Probe F298B

F298B was prepared from F296B upon treatment with 20% fuming sulfuric acid in a solution of concentrated sulfuric acid. Yields were 79% respectively.

EXAMPLE 11

Synthesis of Probe F305B

F305B was synthesized as shown below.

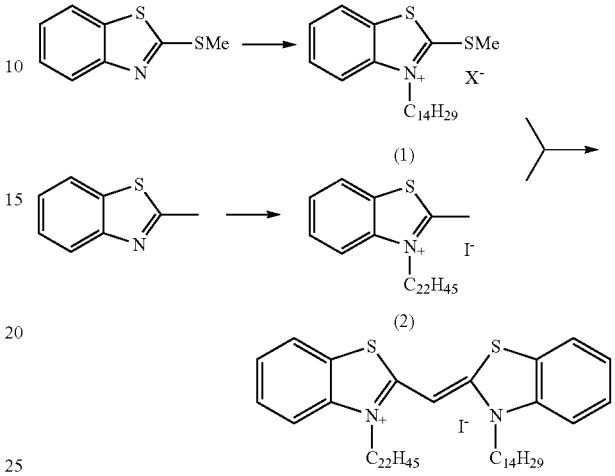

Reaction of 2-methylthio-benzthiazole with tetradecyl-4-chlorobenzene sulphonate ester at 120° C. for 2 h provides salt (1) and reaction of 2-methylbenzthiazole with docosanyl-4-chlorobenzene sulphonate ester at 120° C. for 12 h followed by treatment with saturated potassium iodide provides salt (2). Coupling of (1) and (2) with DBU in DMF at 60-70° C. for 3-4 h then provides F305B which is purified by recrystallization and chromatography.

EXAMPLE 12

Synthesis of Probe F306B

Step 1:

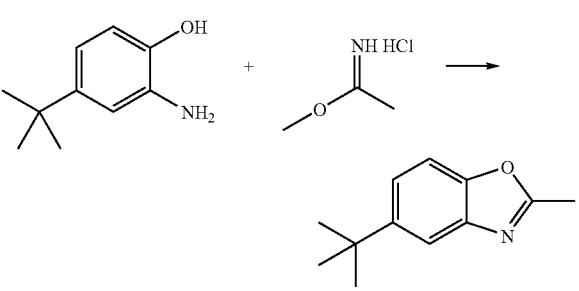

In a 100 ml round bottom flask was placed 7.25 g (0.044 mol) of 2-Amino-4-tert-butylphenol, (Aldrich Cat #193282) with 6.0 g (0.055 mol) of Methyl acetimidate hydrochloride (Aldrich Cat #254940) with 50 ml of MeOH. This was refluxed for 4 hours. Then the MeOH was removed under vacuum. This was separated between 50 ml of ether and 50 ml of water. The ether was separated, dried, and removed under vacuum. Then 50 ml of hexanes was added to the resulting solid. Remaining 2-Amino-4-tert-butylphenol was insoluble in hexanes and was removed by filtration. The remaining oil was chromatographed using 2% MeOH/$CH_2Cl_2$ to provide 5-tert-butyl-2-methylbenzoxazole (Yield=2 g, 24%).

Step 2:

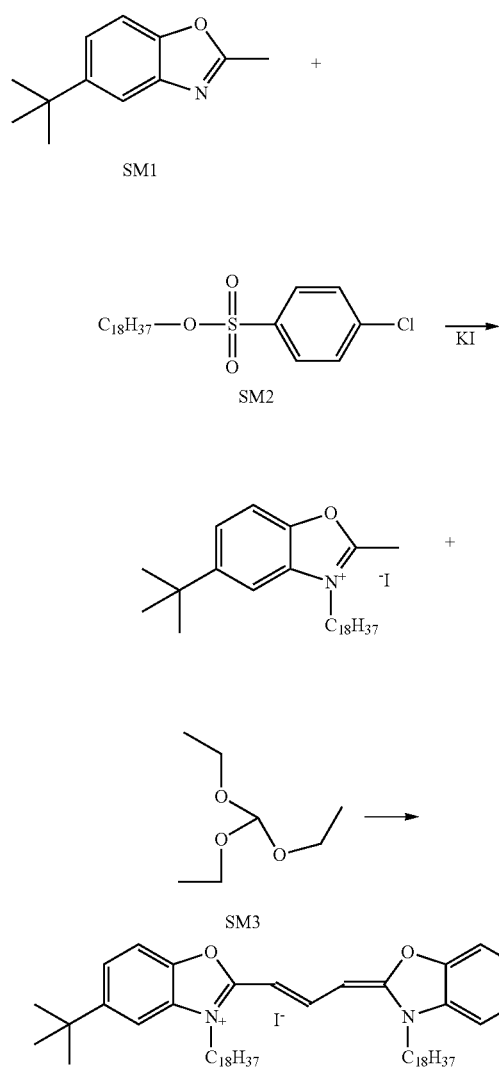

In a 100 ml round bottom flask was placed 2 g (0.0106 mol) of SM1 and 4.7 g (0.0106 mol) of SM2 under argon. This was heated at 150° C. for 4 hours. Then the oil bath was allowed to cool to 120° C. and 4.71 g (0.0318 mol) of SM3 and 20 ml of anhydrous. pyridine was added under argon and refluxed for 2 hours. After cooling to room temperature the reaction mixture was poured into 100 ml of a 5% KI solution and placed in 0-5° C. refrigerator overnight. The residue that remained was washed with 2×100 ml of water and chromatographed using 5% MeOH/CH$_2$Cl$_2$ to provide PTIR306 (Yield=840 mg, 7%).

EXAMPLE 13

Synthesis of Probe F304B

This compound was made in an analogous fashion to PTIR306 but using hexadecyl-4-chlorobenzene sulphonate ester as SM2 instead of octadecyl-4-chlorobenzene sulphonate ester.

EXAMPLE 14

Synthesis of Probe F308B

Step 1:

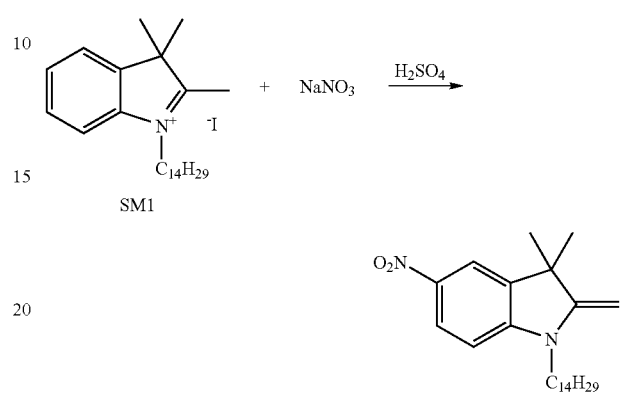

In a 25 ml round bottom flask was placed 2 g (0.00365 mol) SM1 with 15 ml H$_2$SO$_4$. This was stirred in an ice bath for 15 minutes then 0.3 g (0.00365 mol) NaNO$_3$ was added all at once. After stirring for 30 minutes in an ice bath the reaction mixture was stirred at room temperature for 3 hours. This was then poured over 50 grams of ice. NaCl was then added with stirring until saturated. A brown solid separated. Most of the waster was decanted. The solid was dissolved in CHCl$_3$ and washed twice with 50 ml of H$_2$O. The CHCl$_3$ was dried with sodium sulfate and removed under vacuum. The residue was chromatographed on silica gel eluting with 10% MeOH/90% CH$_2$Cl$_2$ to provide the nitro product (Yield=1.12 g, 77%).

Step 2:

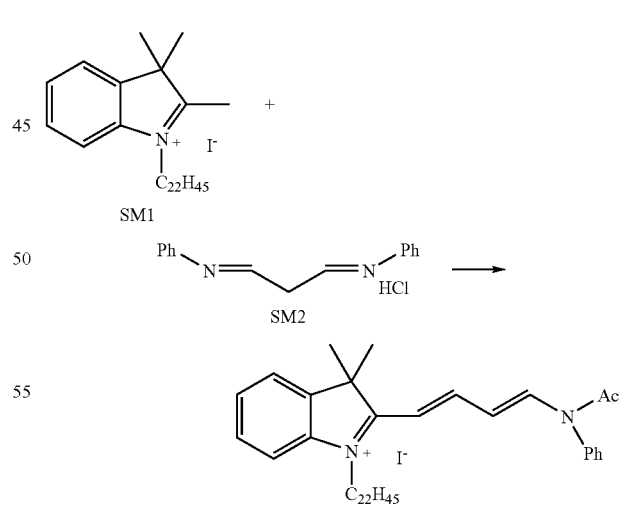

In a 50 ml round bottom flask was placed 1 g (0.0017 mol) of SM1 and 0.46 g (0.0017 mol) of SM2 with 25 ml of Ac$_2$O. This was refluxed in a preheated oil bath at 150° C. for 1 hour. This was then poured into 100 ml of 10% KI and placed in the refrigerator overnight. The resulting solid was used in the next step without purification Step 3:

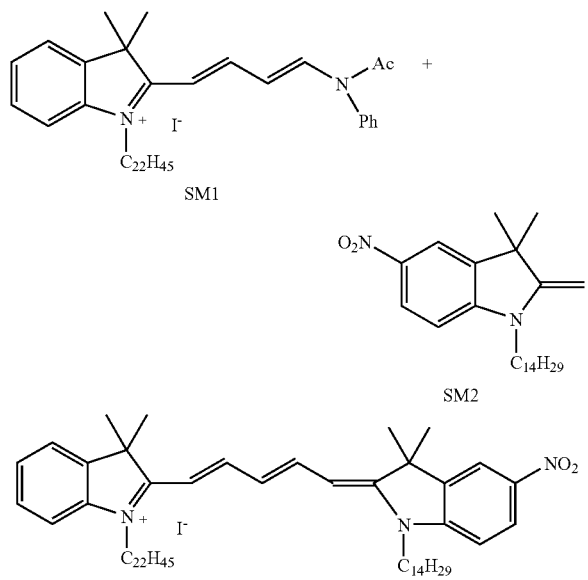

In a 100 ml round bottom flask was placed 1.38 g (0.0018 mol) of SM1 and 0.72 g (0.0018 mol) of SM2 with 50 ml of $CH_2Cl_2$ and the mixture refluxed for 1 hour. This was then placed on 75 g of reverse phase silica flushing with 10% $H_2O$/90% MeOH and 0.1% TFA until all the brown color was off. The column was then eluted with 100% MeOH/0.1% TFA to furnish pure product (Yield=0.29 g, 16%).

EXAMPLE 15

Synthesis of Probe F317B

Step 1:

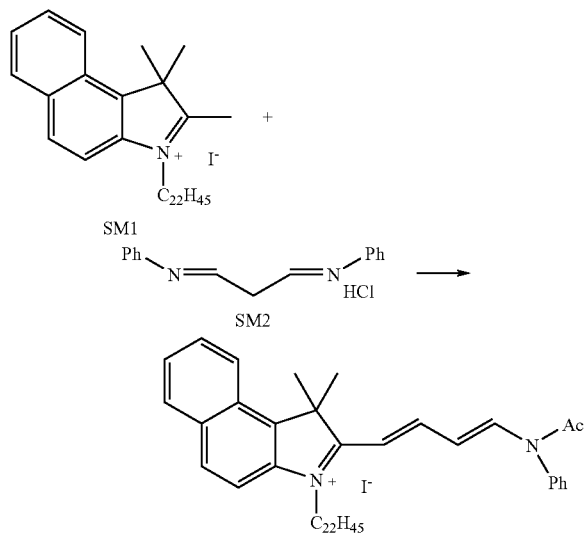

In a 100 ml round bottom flask was placed 5 g (0.0068 mol) of SM1, 1.75 g (0.0068 mol) of SM2 and 60 ml of $Ac_2O$. This was heated at 150° C. for 1 hour in a preheated oil bath. This was then poured into 300 ml of a 10% KI solution and then placed in the refrigerator overnight. The solid was collected, dissolved in $CH_2Cl_2$, dried with sodium sulfate and removed under vacuum. Product was used as is in step 3.

Step 2:

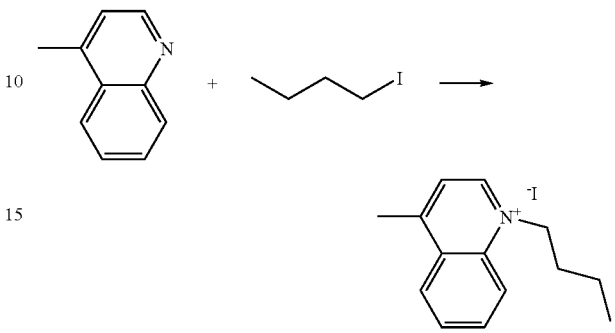

In a 50 ml round bottom flask was placed 2.86 g (20 mmol) of lepidine and 4.04 g (22 mmol) of 1-iodobutane. The reaction was then heated to reflux overnight. The solution was then taken up in 40 ml of $CH_2Cl_2$ and washed with 40 ml of 5% $Na_2CO_3$ and then 2×40 ml of $H_2O$. The organic layer was dried over sodium sulfate, filtered and concentrated under vacuum to provide the product. (Yield=6 g, 92%).

Step 3:

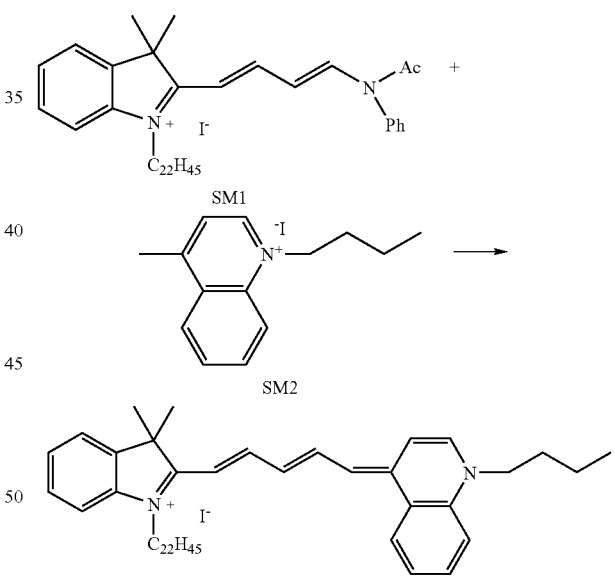

In a 100 ml round bottom flask was placed 2.4 g (0.003 mol) of SM1, 0.98 g (0.003 mol) of SM2, 0.45 g (0.003 mol) of DBU with 50 ml of EtOH. The reaction mixture was then refluxed for 1 hour with stirring. After this time heating was stopped and the mixture stirred overnight. The EtOH was then removed under vacuum and the resulting material was placed onto 50 g of reverse phase silica. The column was eluted with 20% $H_2O$/80% MeOH+0.1% TFA initially and then with 100% MeOH+0.1% TFA. Pure fractions were collected and the concentrated. The resulting material was dissolved in $CH_2Cl_2$, dried over sodium sulfate, filtered, and concentrated under vacuum to provide the product (Yield=156.6 mg, 6%).

EXAMPLE 16

Synthesis of Probe F319B

Step 1:

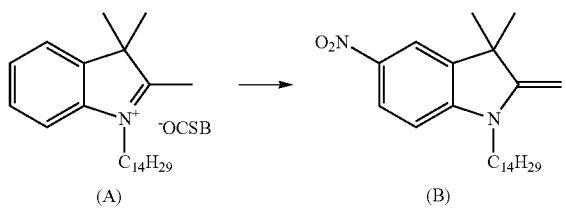

In a 100 ml round bottom flask was placed 4.86 g (0.88 mmol) of N-tetradecyl-2,3,3-trimethylindolinium 4-chlorobenzenesulfonate salt (A) and 50 ml of $H_2SO_4$. This solution was stirred in an ice bath for 15 minutes then 0.75 g (0.88 mmol) of sodium nitrite was added. After 30 minutes of stirring in an ice bath the reaction mixture was stirred at room temperature for 3 hours. It was then poured over 100 g of ice and once the ice melted, sodium chloride was added with stirring until a saturated salt solution was obtained. A brown solid separated and most of the water was decanted. The resulting solid was dissolved in 200 ml $CHCl_3$ and washed twice with 100 ml of $H_2O$. The $CHCl_3$ was dried over sodium sulfate and concentrated under vacuum. The residue was chromatographed on silica gel eluting with 10% MeOH/$CH_2Cl_2$ to provide 1.7 g of product (B). Yield=48%.

Step 2:

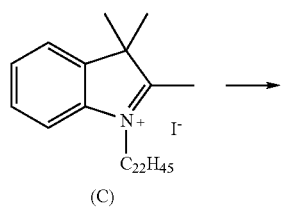

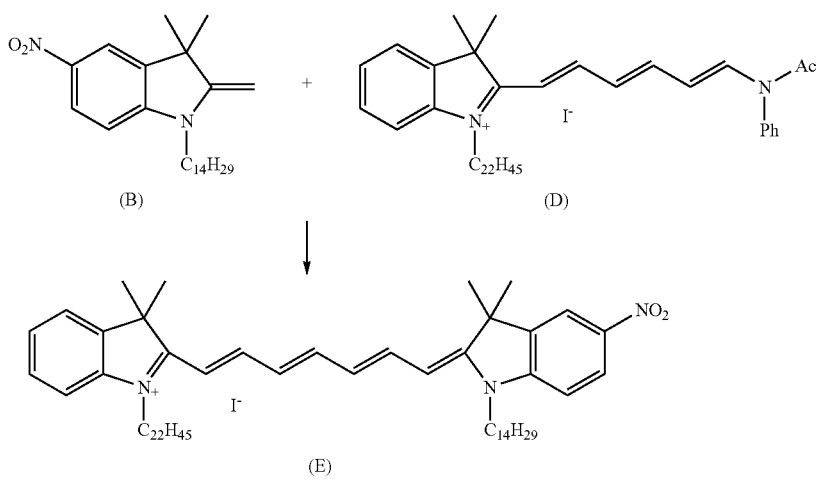

In a 100 ml round bottom flask was placed 50 ml of $Ac_2O$ with 2 g (3.36 mmol) of N-docosanyl-2,3,3-trimethylindolinium iodide (C) and 1.05 g (3.7 mmol) of glutaconaldehyde-dianil hydrochloride. This mixture was refluxed for 2 hours at 150° C. in a preheated oil bath. It was then allowed to cool to room temperature and poured into 200 ml of a 10% KI solution. The resulting solid was filtered off. The solid was dissolved in $CH_2Cl_2$ and the residual water removed by separation. The organic phase was concentrated and the resulting 2.64 g of material (D) used without any further purification.

Step 3:

In a 50 ml round bottom flask was placed 25 ml of $CHCl_3$ with 0.792 g (1.0 mmol) of (D) and 0.4 g (1.0 mmol) of (B). This was refluxed for 1 hour, then allowed to cool. The solvent was removed under vacuum. The residue was placed on a regular phase silica gel column and the column flushed with 1 L of 30% EtOAc/Hexanes, followed by 100% $CH_2Cl_2$, and then finally with 10% MeOH/$CH_2Cl_2$ to remove the product. The resulting material was further purified using 75 g of C18 reverse phase silica and eluting with 10% $H_2O$/MeOH/0.1% TFA followed by 100% MeOH/0.1% TFA. 90 mg of (E) was obtained (8.5% yield).

EXAMPLE 17

Absorbance/Emission Spectra

Referring now to Tables 1 and 2, there are shown the absorbance and emission maxima of some example compounds of the present invention. Absorption and Fluorescence spectra were run using 0.25 μM solutions in ethanol on a Jasco, Inc. UV-530 UV/VIS spectrophotometer and FP 750 spectrofluorometer, respectively. Spectral properties are summarized in Table 1 and Table 2. Approximate extinction coefficients were estimated from the absorbance scans by dividing the maximum absorbance by the nominal concentration (25 μM).

TABLE 1

| Compound # | Abs Max | Extinction Coefficient ($M^{-1}cm^{-1}$) | Flourescence Ex Max | Fluorescence Em Max |
|---|---|---|---|---|
| F277A | 788 nm | 205,400 | 790 nm | 814 nm |
| F279A | 646 nm | 229,500 | 649 nm | 668 nm |
| F280A | 647 nm | 185,700 | 650 nm | 688 nm |
| F283A | 646 nm | 200,700 | 650 nm | 666 nm |
| F284A | 646 nm | 193,700 | 650 nm | 665 nm |
| F285A | 646 nm | 192,900 | 650 nm | 650 nm |
| F288A | 658 nm | 215,350 | 658 nm | 679 nm |
| F289A | 655 nm | 223,500 | 656 nm | 674 nm |
| F291A | 789 nm | 209,100 | 798 nm | 815 nm |
| F301A | 750 nm | 199,300 | 750 nm | 771.5 nm |

TABLE 2

| Compound # | Abs Max | Extinction Coefficient ($M^{-1}cm^{-1}$) | Flourescence Ex Max | Fluorescence Em Max |
|---|---|---|---|---|
| F295B | 650 nm | 259,000 | 652 nm | 669 nm |
| F296B | 654 nm | 256,000 | 654 nm | 670 nm |
| F297B | 651 nm | 239,000 | 652 nm | 670 nm |
| F298B | 655 nm | 241,000 | 655 nm | 672 nm |
| F299B | 647 nm | 178,000 | 650 nm | 664 nm |
| F300B | 657 nm | 197,000 | 650 nm | 664 nm |
| F305B | 425 nm | 81,200 | 420 nm | 461 nm |
| F304B | 493 nm | 160,000 | 494 nm | 508 nm |
| F306B | 492 nm | 135,000 | 493 nm | 508 nm |
| F308B | 649 nm | 134,610 | 493 nm | 671 nm |
| F317B | 718 nm | 149,000 | 652 nm | 771.5 nm |
| F319B | 743 nm | 112,500 |  | 776 nm |

EXAMPLE 18

Chemical Stability of FR/NIR Probes

Chemical stability of example compounds of the present invention when stored at room temperature as a solid or as a 1 mM solution in ethanol were determined by HPLC using the same conditions as above. Integration of the peaks detected for example compounds of the present invention at 260 nm was used to estimate chemical stability. Certain compounds tested displayed <5% change in HPLC purity when held as a solid at room temperature for approximately two months and when held as a 1 mM liquid solution in ethanol at room temperature for approximately one month.

EXAMPLE 19

Photostability of FR/NIR Probes

The photostability of example compounds of the present invention when stored in solution for 24 hours under ambient fluorescent lighting is represented in Table 3. 1 mm solutions of the indicated probes in >60% ethanol were placed under normal fluorescent room lighting. Aliquots were taken from each sample shortly after preparation and the absorbance measured at the absorbance maximum for example compounds. The absorbance of each sample was again measured after 24 hours at room temperature under ambient fluorescent light. Certain compounds tested displayed <20% photobleaching.

EXAMPLE 20

Solubility of FR/NIR Probes

Effects of the various combinations of asymmetrical and symmetrical side chains and methene bridges on the solubility of the compounds of the present invention were examined. Solubility in a commercially available probe diluent. Diluent C, was also tested. Triplicate 1:50 dilutions of stock 1 mM probe solutions were made in either ethanol or test diluent. After 30 minutes at room temperature solutions were centrifuged at 10,000×g for 10 minutes to remove any microagregates and 100 ml aliquots were transferred to 2.0 ml of ethanol for absorbance determinations. Results are expressed as % of absorbance obtained from a control diluted in 100% ethanol as shown in Table 3. Based on the teachings of Leung et al. and on solubility specifications found on Sigma Certificates of Analysis for the commercial diluent (diluent supernatant absorbance at 30 minutes at least 60% of ethanol supernatant absorbance after 30 minutes), a preliminary specification at least 60% of the ethanol control was set as a surrogate for solubility sufficient to achieve cell labeling with S/N ratios greater than 100 and to minimize potential problems with brightness or reproducibility of labeling. Certain example compounds were soluble after 30 minutes in Diluent C.

TABLE 3

| Compound # | Dye Type FR: 600-700 nm NIR: 700-900 nm | Solubility >60% of EtOH Control @ 30 min |
|---|---|---|
| F276A | NIR | 84% |
| F277A | NIR | 95% |
| F283A | FR | 82% |
| F288A | FR | 88% |
| F289A | FR | 70% |
| F290A | NIR | 67% |
| F291A | NIR | 92% |

Diluent C is a commercially available isotonic salt-free vehicle (Sigma-Aldrich Chemical Company) that is commonly used. This example demonstrates that the modified asymmetrical probes of the present invention are soluble in commercially available membrane probe diluents. In addition, it shows that useful levels of cell labeling can be obtained even when solubilities in iso-osmotic diluents are less than those taught by Horan et al.

EXAMPLE 21

Characterization of Violet Probe Effects on Cell Viability, Cell Growth, and S/N Ratios U937 cells were stained at a concentration of $10^7$ cells/ml with increasing concentrations of probe by rapidly admixing 2× cells suspended in Diluent C with 2× probe in Diluent C. After 5 minutes at room temperature, the staining was stopped by the addition of cell culture medium. Cells were then washed thoroughly and cultured under standard conditions for 22-24 hours. Cell numbers were compared to those in a control culture treated with diluent alone.

Maximum Tolerated Concentration (MTC) of F305B was found to be 20 micromol/L for cultured U937 cells stained with commercially available reference dye (PKH26) or with F305B at each dye's MTC showed comparable growth for when monitored daily for 4 days (approximately 4 cell doublings). Cells labeled with both dyes were also monitored daily for changes in mean fluorescence intensity (MFI), using a FACSAria flow cytometer with 488 nm excitation for PKH26 and 405 nm excitation for F305B. The correlation between increasing cell count (cell growth) and decreasing fluorescence intensity (dye dilution) was also found to be comparable for F305B and PKH26, indicating that F305B, like PKH26, has excellent membrane retention properties and is suitable for cell proliferation monitoring using the dye dilution method. As expected, F305B had a lower signal:noise ratio at T0 than PKH26, due to higher levels of cellular autofluorescence in the ultraviolet and violet range. However, initial MFI's were high enough to detect at least 4 and possibly 5 or 6 cell doublings before the fluorescence intensity distribution of labeled cells began to overlap substantially with that of unstained cells. Color overlap of F308B into filter windows used for detection of 488 nm or 633 nm excited dyes was minimal. Since 405 nm excited dyes are less commonly available than 488 nm and 633 nm excited dyes of this nature were therefore deemed useful, despite their somewhat lesser signal:noise ration, for providing increased flexibility in choice of spectral window to be used for monitoring membrane labeled cells and their proliferation.

Maximum Tolerated Concentration (MTC) of F308B was found to be 15 micromol/L for cultured U937 cells (a continuous myelomonocytic cell line) labeled in Diluent C according to the method described above U937 cells stained with commercially available reference dye (PKH26) or with F308B at each dye's MTC showed comparable growth for when monitored daily for 4 days (approximately 4 cell doublings). Cells labeled with both dyes were also monitored daily for changes in mean fluorescence intensity (MFI), using a FACSCalibur flow cytometer with 488 nm excitation for PKH26 and 633 nm excitation for F308B. The correlation between increasing cell count (cell growth) and decreasing fluorescence intensity (dye dilution) was also found to be comparable for F308B and PKH26, indicating that F308B, like PKH26, has excellent membrane retention properties and is suitable for cell proliferation monitoring using the dye dilution method. As expected, F308B had a greater signal:noise ratio at T0 than PKH26 due to lower levels of cellular autofluorescence in the far red. Although the cells were followed for only 4 doublings, the dye dilution curve suggested that at least 7-8 and possibly up to 9 cell doublings could be monitored using F308B before the fluorescence intensity distribution of labeled cells began to overlap substantially with that of unstained cells. Color overlap of F308B was minimal in filter windows used for detection of fluorescein or phycoerythin and modest but easily correctable in the filter window used to detect Texas Red or PE-Cy5 tandem conjugate dyes.

Maximum Tolerated Concentration (MTC) of F317B was found to be 20 micromol/L for cultured U937 cells (a continuous myelomonocytic cell line) labeled in Diluent C according to the method described above to a final cell concentration of $1 \times 10^7$ cells/mL. U937 cells stained with commercially available reference dye (PKH26) or with F317B at each dye's MTC showed comparable growth for when monitored daily for 4 days (approximately 4 cell doublings). Cells labeled with both dyes were also monitored daily for changes in mean fluorescence intensity (MFI), using a FACSCalibur flow cytometer with 488 nm excitation for PKH26 and 633 nm excitation for F317B. The correlation between increasing cell count (cell growth) and decreasing fluorescence intensity (dye dilution) was also found to be comparable for F317B and PKH26, indicating that F317B, like PKH26, has excellent membrane retention properties and is suitable for cell proliferation monitoring using the dye dilution method. However, due to the fact that the excitation maximum for F317B is not as well matched to the 633 nm laser as that of F308B, signal:noise ratio was substantially lower for F317B than for F308B and at most 4 cell doublings could be monitored before the fluorescence intensity distribution of labeled cells began to overlap substantially with that of unstained cells. Substantial color overlap was seen for F317B in all filter windows on the FACSCalibur, further indicating that F308B was a better dye for proliferation monitoring at far red wavelengths.

Maximum Tolerated Concentration (MTC) of F319B was found to be 20 micromol/L for cultured U937 cells (a continuous myelomonocytic cell line) when cells were labeled at a final cell concentration of $1 \times 10^7$ cells/mL in Diluent C according to the method described. U937 cells stained with comparable concentrations of the commercially available reference dye (PKH26, 12 micromol/L) or with F319B (12.5 micromol/L) and monitored daily for the next 6 days showed comparable growth. Cells labeled either with PKH26 or with F319B were also monitored daily for changes in mean fluorescence intensity (MFI), using a FACSAria flow cytometer with 488 nm excitation for PKH26 and 785 nm excitation for F319B. The correlation between increasing cell count (cell growth) and decreasing fluorescence intensity (dye dilution) was also found to be comparable for F319B and PKH26, indicating that F319B, like PKH26, has excellent membrane retention properties and is suitable for cell proliferation monitoring using the dye dilution method. F319B had a substantially greater signal:noise ratio at T0 than PKH26 (approx 5x), due in part to lower levels of cellular autofluorescence in the near infrared and in part to the more optimal match between laser line and excitation maximum for this dye than for PKH26. Although the cells could only be followed for 4-5 doublings when labeled with PKH26, at least 6 doublings could be monitored using F319B before the fluorescence intensity distribution of labeled cells began to overlap substantially with that of unstained cells. Color overlap of F319B was minimal in filter windows used for detection of fluorescein, phycoerthyrin (PE), allophycocyanin (APC), and PE-Texas Red, PE-Cy5 or PerCP-Cy5.5 tandem conjugate dyes. Modest but easily correctable overlap was seen in the filter window used to detect APC-Cy7 tandem conjugate dyes, and more significant but still correctable overlap was seen in the filter window used to detect Alexa 700 dye.

The above descriptions and drawings are only illustrative of a preferred embodiment which achieves the objects, features, and advantages of the present invention, and it is not intended that the present invention be limited thereto. Any modifications of the present invention which come within the spirit and scope of the following claims is considered part of the present invention.

I claim:
1. A cyanine dye having the following chemical structure:

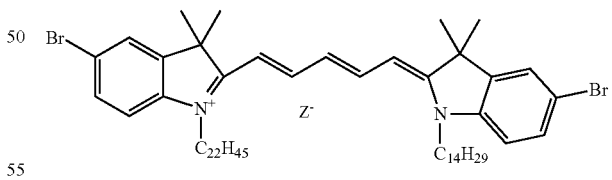

wherein Z is a biologically compatible counterion.
2. The cyanine dye of claim 1, wherein the counterion is selected from the group consisting of chloride, bromide, iodide, sulfate, alkanesulfonate, arylsulfonate, phosphate, perchlorate, tetrafluoroborate, nitrate, an anion of an aromatic carboxylic acid and an anion of an aliphatic carboxylic acid.
3. The cyanine dye of claim 1, wherein the counterion is iodide.
4. An in vivo method for detecting abnormal cell shedding rates of mature surface epithelial cells of a warm-blooded animal, comprising the steps of:

labeling mature surface epithelial cells at a target site of the animal with the cyanine dye of claim 1, and monitoring the site for the presence or absence of the cyanine dye following said labeling step.

5. The method of claim 4, wherein the site is a mucosal surface.

6. The method of claim 4, wherein the mucosal surface lines the surface of the gastrointestinal tract, the respiratory tract, or the genitourinary tract.

7. The method of claim 5 wherein the site is a mucosal surface of the stomach.

8. The method of claim 5 wherein the site is a mucosal surface of the colon.

9. The method of claim 4, wherein cell shedding is detected by observing changes in the level of the cyanine dye at the site at a pre-selected time following said labeling step.

10. The method of claim 4, further comprising the step of exciting the target site with a light source wherein the light source has a wavelength of from about 600 nm to 1000 nm.

11. The method of claim 4, wherein the epithelial cells are labeled by direct application of a labeling composition comprising the cyanine dye to the site.

12. The method of claim 4, wherein said labeling step comprises applying to mature surface epithelial cells at a target side a labeling composition comprising the cyanine dye.

13. The method of claim 12, wherein said monitoring step comprises observing the rate at which the cyanine dye is lost from the target site.

14. The method of claim 12, wherein said labeling composition further comprises a pharmaceutically acceptable vehicle.

15. The method of claim 11, wherein said labeling composition further comprises a pharmaceutically acceptable vehicle.

16. The method of claim 4, wherein the counterion is selected from the group consisting of chloride, bromide, iodide, sulfate, alkanesulfonate, arylsulfonate, phosphate, perchlorate, tetrafluoroborate, nitrate, an anion of an aromatic carboxylic acid and an anion of an aliphatic carboxylic acid.

17. The method of claim 4, wherein the counterion is iodide.

* * * * *